United States Patent [19]

Thomas

[11] 4,008,332

[45] Feb. 15, 1977

[54] MICROCIDE

[76] Inventor: Richard Dean Thomas, 812 N. Euclid St., Fullerton, Calif. 92632

[22] Filed: Dec. 23, 1969

[21] Appl. No.: 884,771

Related U.S. Application Data

[63] Continuation of Ser. No. 658,359, Aug. 4, 1967, abandoned.

[52] U.S. Cl. .............................................. 424/334
[51] Int. Cl.$^2$ ................ A61K 31/115; A61L 13/02
[58] Field of Search ..................... 424/343, 349, 334

[56] References Cited

UNITED STATES PATENTS

| | | | |
|---|---|---|---|
| 2,261,788 | 11/1941 | Wyler ................................. | 260/635 |
| 2,564,366 | 8/1951 | Landau et al. ...................... | 424/675 |
| 3,024,202 | 3/1962 | Jones ................................. | 252/397 |
| 3,629,464 | 12/1971 | Nosler et al. ...................... | 424/334 |

OTHER PUBLICATIONS

Chemical Abstracts, 1934, vol. 28, p. 5039.

Kirk, et al., Encyclopedia of Chemical Technology, 2nd edition, vol. 10, p. 95.
Mendelsohn, Manufacturing Chemist, 1952, p. 191.
U.S.P. XVI, p. 1064, 1960.

*Primary Examiner*—Dale R. Ore
*Attorney, Agent, or Firm*—Albert L. Gabriel

[57] ABSTRACT

A microcidal liquid chemical combination for the controlled release of formaldehyde in intimate association with surfaces to be disinfected. The principal ingredients of the combination are 2-Hydroxymethyl-2-Nitro-1,3-Propanediol (hereinafter for convenience referred to as HNP), the active ingredient for releasing formaldehyde, formalin to prevent premature decomposition of the HNP, a pH adjusting agent to retain the HNP in its active state, and a hydroscopic material to keep the HNP moist for continued activity.

9 Claims, No Drawings

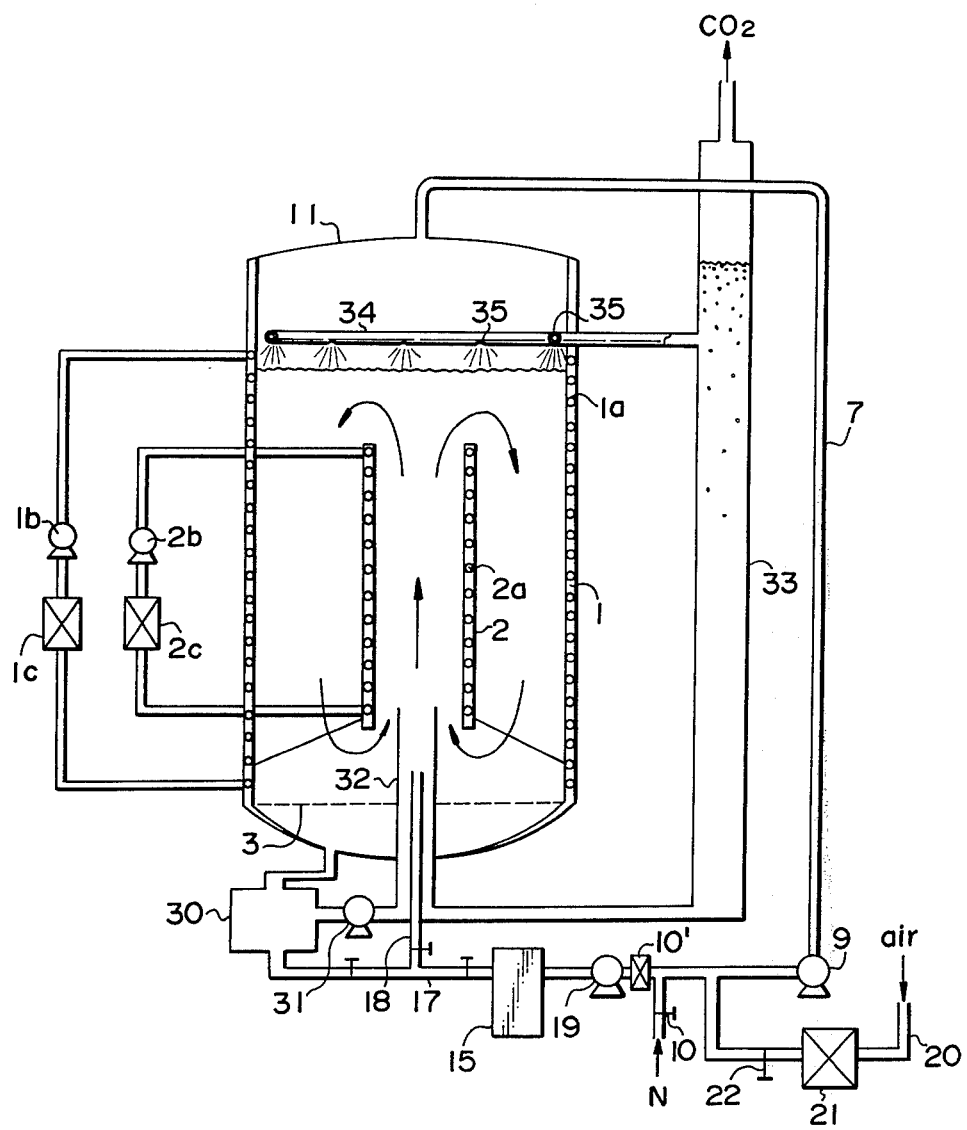

MICROCIDE

This application is a continuation of my application Ser. No. 658,359, filed Aug. 4, 1967, now abandoned.

BACKGROUND OF THE INVENTION

Formaldehyde is presently widely employed as a fumigant for disninfecting animal quarters and equipment, and is currently used in livestock and poultry production. The formaldehyde is applied both as a liquid spary and as a gas.

When used as a spray, formalin (commercial liquid formaldehyde, which is approximately a 37% aqueous solution) is diluted about 1 part formalin to 6 parts water and sprayed onto walls, floors and equipment. This liquid spray has an extremely bad odor, and is very toxic. The operator must use a respirator, and even then the fumes may come through, and can be dangerous.

When the formaldehyde is used as a gas, the enclosure to be fumigated is sealed, or if it is equipment that is to be fumigated, it must be placed in a sealed enclosure. Before the enclosure is sealed, it is wetted down well and the temperature is raised to about 95° F. to 100° F., and also a fan is generally used to circulate the air in the enclosure. It is required that the enclosure, and any part thereof to be fumigated, be wetted down because the formaldehyde is not effective as a gas, and the formaldehyde gas employed in the fumigation must go into solution in the water and then come into contact with the surfaces to be fumigated in order to be effective. Although this practice is used regularly in poultry production and on ranches, it is generally inadequate, and there is no assurance of substantially complete disinfecting as with the liquid formaldehyde spray where the operator can be sure that everything to be fumigated is covered. With the use of formaldehyde gas, there is the advantage that the enclosure is sealed up and the operator can leave the area while fumigation is being accomplished, instead of being directly subjected to the fumigation as where the operator is using the spray. However, in addition to the general inadequacy of the formaldehyde gas treatment, it is flammable and explosive, and some places have burned as the result of its use. Also, it is very difficult to seal any relatively large enclosure to prevent the escape of the formaldehyde gas.

SUMMARY OF THE INVENTION

In view of these and other problems in the art, it is an object of the present invention to provide a novel liquid microcide composition which is useful both as a spray and as a dip, or with any other suitable means for application, to provide the controlled release of formaldehyde in intimate association with the surfaces to be disinfected, to provide effective microcidal activity almost immediately and over and extended period of time.

Another object of the invention is to provide a liquid fumigant of the character described which, by releasing the formaldehyde at a controlled rate directly upon the surfaces being disinfected, produces effective microcidal action without substantial toxicity or objectionable odor such as are normally associated with the use of formaldehyde as a disinfectant.

Another object of the present invention is to provide a liquid fumigant composition of the character described wherein the active ingredient for releasing formaldehyde directly on the surfaces being disinfected is 2-Hydroxymethyl-2-Nitro-1,3-Propanediol (HNP), the release of formaldehyde from the HNP being controlled by the independent addition of formaldehyde, preferably as formalin, into solution to prevent premature decomposition of the HNP, by including a pH adjusting agent in the composition to maintain the HNP at an active level, and by inclusion of a hygroscopic material in the composition for pulling water into the composition to provide the moisture which is necessary to maintain the activity of the HNP.

An additional object is to improve the performance of the composition by including a humectant for retention of water in the disinfectant film during the operation thereof, and by including a wetting agent in the composition to increase penetration when the composition is applied for maximum surface coverage.

A general object of the invention is to provide a novel liquid fumigant which provides all of the advantages of conventional formaldehyde spray or gas fumigation without any of the difficulties or dangers normally associated therewith, and with the additional advantages of microcidal activity over an extended period of time if desired, and of control over the length of time that the microcidal activity prevails for a wide range of time periods, as for example, from a matter of hours on the one hand to days or weeks or even months, on the other hand.

Other objects and advantages of the present invention will appear during the course of the following part of the specification.

DETAILED DESCRIPTION

The active material, HNP, is employed in the present composition of matter because it has the unique characteristic of yielding formaldehyde gas upon decomposition. Its decomposition to yield formaldehyde gas commences when the pH of the solution is above about 4. The higher the pH the faster this decomposition. In order for the release of formaldehyde gas from HNP decomposition to be adequate for the present purpose, the pH of the solution containing the HNP should not be substantially below about 7. On the other hand, if the pH is too high, then decomposition of the HNP will be too rapid for adequate control according to the present invention, so that the pH of the solution of the invention when used should not be substantially higher than about 8.

Accordingly, a pH adjusting agent is included in the present composition, which will both raise the pH of the solution so that it is not substantially below about 7, and will also buffer the solution to maintain or stabilize this pH. While any of a variety of bases and buffering agents may be employed, it is preferred to employ a base which has inherent buffering capability, such as a phosphate base. The presently preferred pH adjusting agent, which is both a base and a buffering agent, is sodium phosphate, tribasic (trisodium phosphate). Potassium phosphate has also been found to be satisfactory, and additionally sodium carbonate has been used effectively as the base.

In preparing the present composition of matter, it has been found that for a period of several days after the composition is formulated the pH will fade back down before it becomes stabilized. The presently preferred final pH for the product is approximately 7.4, but it has been found that to establish this final pH of about 7.4, it is necessary to adjust the pH when the composition is formulated to approximately 8.1, and then the pH will fade back to the approximately 7.4 value desired. In practice, the pH is adjusted to from about 8.0 to about 8.2, and then it will fall back and stabilize at a pH of from about 7.3 to about 7.5. In tests, it has been found that if the pH is adjusted to above about 8.7, it will still fall back to in the neighborhood of 7.4 or 7.5, but the HNP will be so active at the higher pH that it will give off a substantial amount of formaldehyde, thereby impairing the final product.

Formaldehyde is added to the present solution independently of the formaldehyde that is released from the HNP upon its decomposition, as a stabilizer. Without stabilization, the HNP when adjusted to the proper pH range for the present invention will decompose so as to lose its effectiveness within a relatively short period of time. While this decoposition is not fully understood, it appears that the HNP in the pH adjusted composition will decompose and release formaldehyde which, in the composition, will oxidize to formic acid, and this process appears to continue to a point at which the solution is ineffective for the present purpose. However, by means of the separate addition of formaldehyde, preferably as formalin, the release of formaldehyde from the HNP in the contained solution is quickly stabilized by the additional formaldehyde, with an equilibrium being reached which prevents further decomposition of the HNP. In this manner, the HNP is preserved in the solution and is available for the active release of formaldehyde when the solution is applied as thin film as by spraying or dipping or otherwise. When the solution is thus applied as a tin film, this stabilizing effect of the added formaldehyde is relieved because the added formaldehyde can then be given off from the surface of the film, and in fact provides some additional formaldehyde at the surface which is being disinfected so as to increase the activity of the composition in its early phase of disinfecting operation.

The hygroscopic material is an essential ingredient in the combination to allow the HNP to continue its activity in releasing formaldehyde gas over a substantial period of time. This is because the thin liquid film which is sprayed or otherwise applied would otherwise quickly dry out, even under high humidity conditions, causing premature arresting of the activity of the HNP. For the purpose of the present applicaion, a hydgroscopic material is hereby defined as a material which will pull in or take on moisture from the surrounding atmosphere. The hygroscopic material may be any conventional hygroscopic material, and may if desired by a deliquescent material, although deliquescence is not required. Examples of hygroscopic material which have been found in practice to be suitable for the present composition are aluminum chloride ($AlCl_3$), zinc chloride and calcium chloride. This inclusion of hygroscopic material in the combination allows the HNP to continue its decomposition activity and release of formaldehyde gas in its direct contact with the surfaces being disinfected to substantial completion of the activity. Theoretically, from every mole of the HNP there will be three full moles of formaldehyde released from the thin film of composition that is sprayed or otherwise applied to the surfaces being disinfected. However, in practice the amount of formaldehyde will not reach this theoretical quantity, although it will be sufficient for highly effective microcidal activity over a sustained period of time.

Preferably a humectant is also included in the composition, although this does not appear to be a necessary ingredient. For the purpose of this application, a humectant is defined as material which has the property of holding moisture in the solution. While any suitable humectant can be utilized, glycerol (i.e., glycerin) has been found it practice to be particularly suitable humectant.

A wetting agent or surfactant also is desirable as one of the ingredients in the present composition, although this also does not appear to be a necessary ingredient. The wetting agent assists penetration of the solution into dust, manure, wood cracks, etc., thereby improving the overall microcidal effect of the composition in operation. Although any suitable wetting agent or surfactant can be utilized, examples of wetting agents which have been found to be satisfactory in use are alkyl-dimethyl-benzyl-ammonium chloride, sodium alkyl sulfonate, and the commercial product "All".

A further ingredient which may be included in the composition, but which is not required, is a dyestuff to give the product color. It has been found in practice that otherwise, when the commercial concentrate form of the composition is diluted for application as a spray, it cannot be discerned either by color or by odor. By adding a dyestuff, when the concentrated solution is diluted for application, the operator can then be sure that the composition of the invention is present in the solution which he is using.

Testing of various relative proportions of HNP and formalin in the composition show that the minimum satisfactory ratio by weight of formalin to HNP is about 1 part formalin to 10 parts HNP. If the proportion of formalin is less, then the HNP appears to decompose at a regular rate in the bottled solution, so that the product will not be fully effective when uitlized as a spray or the like. Accordingly, it is preferred to employ a formulation wherein the weight ratio of formalin to HNP is at least 1:10. A presently preferred formulation employs approximately 1 part of formalin to 4 parts of HNP.

Because of the fact that a wide variety of hygroscopic materials can be employed, and in general each of these will have different hygroscopic activity, it is not practical to define the minimum quantity thereof by weight, except by reference to a particular hygroscopic material which has been tested. At this time, the most active hygroscopic material which has been tested in the composition of the present invention is zinc chloride, and it has been found that the minimum effective quantity thereof is about 1 part by weight per 275 parts by weight of HNP.

As a general guideline, the composition should contain a sufficient amount of the hygroscopic material to allow substantially complete decomposition of the HNP; i.e., to pull in adequate moisture to keep the HNP active through its full cycle of decomposition to produce formaldehyde gas.

A formulation of ingredients according to he present invention which has produced excellent results in practice, expressed as percent by weight of ingredient other than water, is as follows:

| | |
|---|---|
| HNP | 73.32% |
| Formalin | 18.15% |
| Alkyl-dimethyl-benzyl-ammonium-chloride (ADBAC) | 6.29% |
| Aluminum chloride | 1.05% |
| Glycerol | 0.63% |
| Sodium phosphate, tribasic | 0.56% |
| Total | 100.00% |

A corresponding satisfactory final formula, ready for spraying, is as follows:

| | |
|---|---|
| HNP | 2.100 gm |
| Formalin | .520 gm |
| ADBAC | .180 gm |
| Aluminum chloride | .030 gm |
| Glycerol | .018 gm |
| Sodium phosphate, tribasic- | .016 gm |
| Water | to one liter |

In this liquid solution, ready for spraying, water comprises 99.924% of the solution, and the remaining ingredients comprise 00.076% of the solution. Such a dilute solution, while providing an excellent microfilm of the composition for disinfectant purposes, is too dilute to be a practical commercial product, and accordingly it is preferred to provide the composition in a concentrate solution, which can be prepared as follows: dissolve 210 gm of HNP in 210 ml of distilled water. Add 52 gm of formalin with stirring. Add 36 gm of a 50% solution of alkyl-dimethyl-benzyl-ammonium-chloride, 10 gm of a 30% solution of aluminum chloride and 1.8 gm of glycerol with stirring. Add distilled water to 900 ml. Adjust pH to 8.1 with a 2.5% solution of sodium phosphate. Add distilled water to one liter.

Such a commercial concentrate solution may for some purposes be employed without dilution, as indicated hereinafter, but normally will be diluted with ordinary tap water. A typical dilution ratio for most ordinary purposes, as for example for spraying housing, poultry and livestock trucks, feed trucks, and general ranch equipment, is 1 oz. of the aforesaid commercial concentrate per gallon of tap water, which is a ratio of 1:128. Although the rate of decomposition will vary according to temperature, typically this 1 oz. per gallon spray will provide a microfilm of the composition which remains active about a day in relatively hot weather when exposed in an external environment. However, where used in housing which is cool and closed, where evaporation is much slower, the composition may last for a week or even several weeks.

The composition begins killing microorganisms immediately upon contact, and reaches its maximum effectiveness in approximately ten minutes, and then remains highly effective over the life cycle of decomposition of the HNP in the combination.

The duration of activity of the applied composition can be controlled by varying the concentration of the spray. Thus, providing a more concentrated spray will produce a thicker film of the composition, which will have a proportionately large quantity of HNP therein, and therefore will remain active in general a proportionately longer time, since there will be approximately the same surface area for release of formaldehyde. For example, where a longer period of operation is desired, typically 3 to 4 oz. of the concentrate will be mixed with a gallon of water for spraying.

Another situation where a more concentrated spray is desired is where it is preferred not to apply too much water to the environment, but a substantial film thickness is nevertheless desired. For example, in the environmentally controlled houses for livestock and poultry production which are generally made with plywood that is painted aluminum, and an excess of water might damage the structure, instead of the 1 oz. of commercial concentrate per gallon, it is preferable to use about 4 oz. of the concentrate per gallon and spray on proportionately less of the solution. Another situation where it is desirable to keep the amount of moisture down is in spraying the insides of trucks used for hauling chickens or livestock, so that for such purposes 3 to 4 oz. of the concentrate per gallon of water provides about the right thickness of film right thickness of film.

Although the high toxicity of conventional formaldehyde application makes it unusable for direct application to eggs at the hatchery level, it is nevertheless important to provide a continued and controlled fumigation of eggs during the entire hatching cycle, which for a chicken takes 21 days, and for a turkey takes 28 days. The present composition has been found particularly suitable for this purpose because of its substantially non-toxic character and its ability to provide sustained fumigation over long periods of time.

Although the composition of the present invention can be sprayed on the eggs in almost any desired concentration without damaging the eggs, it has been found that it possible even to use it in its concentrate form without damaging the eggs or the chick. Many chicks and turkey poults are lost because of the presence of bacteria which can be disposed of by the present composition. Typically, out of every 100 chick eggs there is a production of only about 70 chicks, while with turkey eggs there is a production of only about 65 turkey poults, and a large percentage of these failures are the result of bacterial action which can be controlled by the present invention. Whenever an egg is laid it is moist with a mucous coating which contains various types of intenstinal organisms. When laid, the egg has a temperature of about 105° and as the shell cools it contracts and pulls some of these organisms right through the shell membrane and into the inside of the egg, and the presence of such bacteria in the egg can kill the embryo.

Another phase of hatching in which bacterial action is dangerous is when the chick or turkey poult hatches, because of the presence of an open navel which is a ready source of infection, either from bacteria inside of the shell or bacteria immediately outside of the shell.

One way of controlling such bacteria which are detrimental in the hatchery is to spray a sufficiently concentrated solution of the present invention to last during the entire 21 days to hatch a chick or 28 days to hatch a turkey poult. Alternatively, the eggs can first be sprayed with the solution when they are into the incubator or setter, wherein a chick eggs are kept for 16 days, and then they can be again sprayed when they are transferred to the hatcher where they remain for 5 days.

Another way in which the invention can be utilized in a hatchery that has shown particularly good results is to dip the eggs in the composition of the present invention preferably within one hour, and at a maximum within two hours after the eggs are laid, providing the solution of the invention at a substantially lower temperature than the eggs, as for example about 30° F. below the temperature of the eggs at the time they are dipped. This temperature differential will shrink the surface of the egg and pull the composition of the invention inside of the egg shell. It has been found in practice that even the commercial concentrate solution set forth herein-above can be used in this manner without damaging the embryo, because of its substantially non-toxic characteristics. By this means, the composition of the invention will remain active until hatching occurs, and will be disposed in an optimum region for protecting the embryo from bacterial damage.

The composition of the present invention is also useful for direct application to animals. As an example of this, where animals such as sheep are infected with, or should be protected from foot rot, it has been the practice to have the animals walk through a formaldehyde bath, but this has proven to be very dangerous to the animals because of the high toxicity of the formaldehyde. With the present invention, such a bath will apply a coating film of the composition which will produce the desired formaldehyde fumigation, but because of its substantially non-toxic characteristics it will not be in any way dangerous to the animals.

While the present invention has been described herein in what is conceived to be the most practical and preferred embodiment, it is recognized that departures may be made therefrom within the scope of the invention, which is therefore not to be limited to the details disclosed herein, but is to be accorded the full scope of the claims.

I claim:

1. A microcidal solution for the release of formaldehyde on surfaces to be disinfected comprising water, 2-hydroxymethyl-2-nitro-1,3-propanediol as an active ingredient for releasing formaldehyde, a pH adjusting agent to adjust the pH of the solution in the range of from about 7 to about 8.0 to maintain said active ingredient at a stage of activity at which it will release formaldehyde at a desired rate, formaldehyde in said solution in a ratio of at least about one part by weight, calculated as formalin, to about ten parts by weight of said active ingredient to prevent premature decomposition of said active ingredient prior to the application of the solution to said surfaces, and a hygroscopic material in an amount sufficient to pull in adequate moisture to allow substantially complete decomposition of the said active ingredient on said surfaces.

2. The composition of claim 1 wherein said ratio is approximately 1:4.

3. The composition of claim 1 wherein the pH of the solution is in the range of from about 7.3 to about 7.5.

4. The composition of claim 1 wherein glycerol is also present.

5. A liquid microcidal composition comprising the following ingredients: 2-hydroxymethyl-2-nitro-1,3-propanediol; formalin in an amount of at least 1 part by weight to 10 parts by weight of said 2-hydroxymethyl 2-nitro-1,3-propanediol; zinc chloride in an amount of at least about 1 part by weight of said 2-hydroxymethyl-2-nitro-1,3-propane diol; water in an amount sufficient to provide an aqueous solution of the foregoing ingredients; and pH adjusting agent in an amount sufficient to adjust the pH of said solution to about 7.0 to about 8.0.

6. The composition of claim 5 wherein glycerol and alkyl-dimethyl-benzyl-ammonium chloride are additionally present.

7. A method of disinfecting animals, animal quarters, eggs and animal equipment, comprising applying to the surfaces to be disinfected a solution containing water, 2-hydroxymethyl-2-nitro-1,3-propanediol as an active ingredient for releasing formaldehyde, a pH adjusting agent to adjust the pH of the solution in the range of from about 7 to about 8 to maintain said active ingredient at a stage of activity at which it will release formaldehyde at a desired rate, formaldehye in said solution in a ratio of at least about one part by weight, calculated as formalin, to about ten parts by weight of said active ingredient to prevent premature decomposition of said active ingredient prior to the application of the solution to said surfaces, and a hygroscopic material in an amount sufficient to pull in adequate moisture to allow substantially complete decomposition of said active ingredient on said surfaces.

8. A method for disinfecting surfaces by the release of formaldehyde on said surfaces comprising applying to said surfaces a solution containing water, 2-hydroxymethyl-2-nitro-1,3-propanediol as an active formaldehyde releasing ingredient, said solution having a pH in the range of from about 7.3 to 7.5 and containing formaldehyde in a ratio of at least about one part by weight, calculated as formalin, to about ten parts by weight of said active ingredient to prevent premature decomposition of said active ingredient prior to the application of the solution to said surfaces, and a hygroscopic material in an amount sufficient to pull in adequate moisture to allow substantially complete decomposition of said active ingredient on said surfaces.

9. In a method of preparing a solution containing water and 2-hydroxymethyl-2-nitro-1,3-propanediol as an active ingredient for use a microcide by application to surfaces to be disinfected, the improvement comprising adjusting the pH of the solution to about 7.0 to about 8.0, adding formaldehyde to the solution in an amount of at least about one part by weight, calculated as formalin, to about ten parts by weight of said active ingredient to prevent premature decomposition of said 2-hydroxymethyl-2-nitro-1,3-propanediol prior to application of the solution to the surfaces to be disinfected, and adding a hygroscopic material to said solution in an amount sufficient to pull in adequate moisture to allow substantially complete decomposition of said active ingredient on said surface.

* * * * *

UNITED STATES PATENT OFFICE
CERTIFICATE OF CORRECTION

Patent No. 4,008,332          Dated Feb. 15, 1977

Inventor(s) Richard Dean Thomas

It is certified that error appears in the above-identified patent and that said Letters Patent are hereby corrected as shown below:

The sheet of drawing should be omitted.

Signed and Sealed this

Twenty-sixth Day of April 1977

[SEAL]

*Attest:*

RUTH C. MASON
*Attesting Officer*

C. MARSHALL DANN
*Commissioner of Patents and Trademarks*